United States Patent
Green et al.

(10) Patent No.: US 6,471,637 B1
(45) Date of Patent: Oct. 29, 2002

(54) IMAGE ORIENTATION FOR ENDOSCOPIC VIDEO DISPLAYS

(75) Inventors: Daniel Green, Clark, NJ (US); Robert Ibach, Kleeweg; Jan Fablanowski, Donnerstrasse, both of (DE)

(73) Assignee: Karl Storz Imaging, Inc., Goleta, CA (US)

( * ) Notice: Subject to any disclaimer, the term of this patent is extended or adjusted under 35 U.S.C. 154(b) by 40 days.

(21) Appl. No.: 09/666,692

(22) Filed: Sep. 21, 2000

Related U.S. Application Data

(60) Provisional application No. 60/155,850, filed on Sep. 24, 1999.

(51) Int. Cl.$^7$ ............................................. A61B 1/04
(52) U.S. Cl. ................... 600/109; 600/112; 600/137; 600/100; 600/173
(58) Field of Search ............................. 600/109, 112, 600/137, 160, 173; 348/65, 66, 68–70, 75, 82; 356/241.1

(56) References Cited

U.S. PATENT DOCUMENTS 5,677,763 A  * 10/1997  Redmond .................... 356/615

FOREIGN PATENT DOCUMENTS

JP          6-269403    *  9/1994   ............ A61B/1/04

* cited by examiner

*Primary Examiner*—John Mulcahy
(74) *Attorney, Agent, or Firm*—St. Onge Steward Johnston & Reens LLC

(57) ABSTRACT

An apparatus and technique for compensating the display of an image obtained from an endoscope as it is moved through various orientations are described. The endoscope received optical image is converted to an electrical signal with an image sensor that can be a CCD or a CMOS detector. The endoscope has an inertial sensor to sense rotations of the received image about the optical axis of the endoscope and the sensor's output signals are used to rotate either the image or the image sensor. In case of rotation of the image sensor the rotation sensor can be a gyroscope or a pair of accelerometers. In case of a rotation of the image obtained with the image sensor the inertial sensor, which can be an accelerometer or a gyroscope, the image is rotated within a microprocessor for subsequent viewing on a video display. The signal processing to achieve compensatory rotations of the displayed image as an operator of the endoscope moves it about is described.

9 Claims, 12 Drawing Sheets

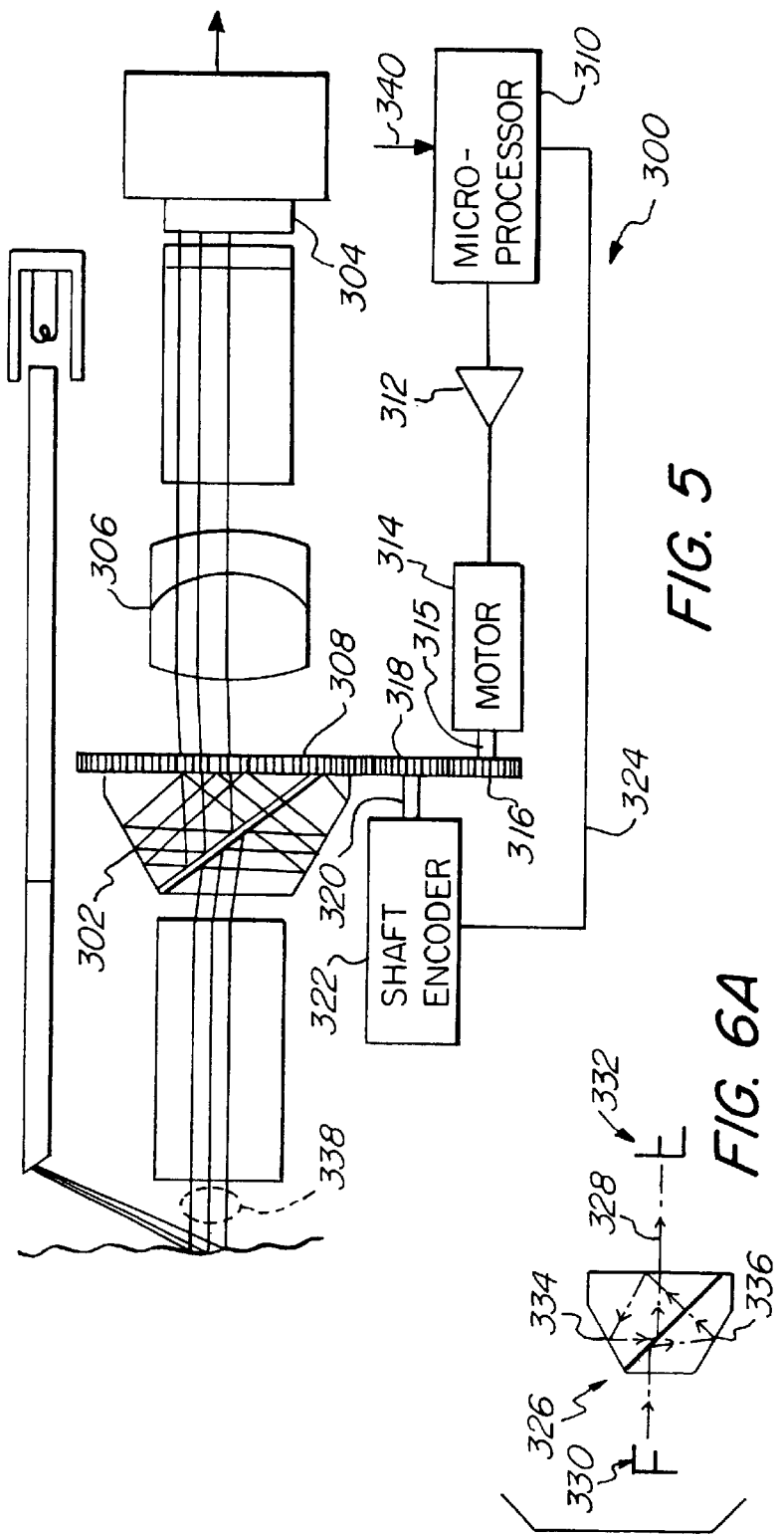

IMAGE ORIENTATION FOR ENDOSCOPIC VIDEO DISPLAYS

CROSS-REFERENCE TO PRIOR APPLICATIONS

This is a continuation in part of patent application Ser. No. 60/155,850 of Chatenever filed Sep. 24, 1999, incorporated herein by this reference, as though set forth in full.

FIELD OF THE INVENTION

This invention relates generally to video displays of images obtained from an endoscope. Specifically, the orientation of the image as viewed on the screen is presented in its actual relationship to the viewer's reference frame.

BACKGROUND OF THE INVENTION

An endoscope is an elongated tubular structure that is inserted into body cavities to examine them. The endoscope includes a telescope with an objective lens at its distal end. The telescope includes an image-forwarding system. In rigid endoscopes it is a series of spaced-apart lenses. In flexible endoscopes it is a bundle of tiny optical fibers assembled coherently to forward the image. This invention is applicable to both types of image forwarding systems.

At the proximal end of the image-forwarding system is an ocular lens which creates a virtual image for direct human visualization. Often a camera means such as a charge coupled device (CCD) chip, is mounted to the endoscope. It receives the image and produces a signal for a video display. A CCD is a semiconductor component that is used to build light-sensitive electronic devices such as cameras and image scanners. Each CCD chip consists of an array of light-sensitive photocells that produce an analog output proportional to the intensity of the incident light.

While surgeons can, and often do, look directly into the endoscope through an ocular lens, it is more common for them to use an attached video camera and observe an image on a video screen. In a surgical or diagnostic procedure, the surgeon the endoscope. He may tilt it, push it in, pull it out, and also rotate it around its mechanical axis. As these manipulations occur to an endoscope with an attached video camera, the camera faithfully relates what it sees, with its own upright axis displayed as the upright axis of the image on the display. This means that if the camera is rigidly fixed to the endoscope, and the endoscope-camera is rotated around its mechanical axis, the displayed image on the monitor will move proportionately and in the opposite direction to that of the endoscope camera. A clockwise rotation of the endoscope-camera through an angle of 45 degrees will cause a counterclockwise rotation of the image on the monitor through an angle of 45 degrees.

That is the very problem. When the image is displayed on the screen and the endoscope is rotated around its axis, it is as though the surgeon must tilt his head to follow it. However, the surgeon is standing up, and the rotating image is distracting to him. What he really wants to see on the screen is an image that is oriented the same as he would see it if he were inside, standing up, with the same upright orientation. Stated otherwise, he would prefer to see what he would see if he were looking directly into the endoscope, instead of viewing a screen. This is impossible when the camera is fixed to the telescope and rotates with it, while the surgeon does not.

In a conventional endoscope and camera arrangement, the camera is usually detachably and rotatably connected to the endoscope. In this arrangement the rotated image on the monitor screen can be righted by manually counter-rotating only the camera such that its orientation is upright. Alternatively, one can avoid this rotated image condition by holding the camera in its upright position and rotating only the endoscope.

Suggestions have been made to decouple the camera from the telescope so the camera can rotate independently of it, using a pendulum to seek the vertical. This seemingly sensible approach runs afoul of conditions imposed by the use of the instrument. Endoscopes are used in close quarters, and their proximal ends must be kept as small and uncluttered as possible. Physical interference with surroundings and with the surgeon's hands must be eliminated or greatly minimized. However, a pendulum to be useful must have a substantial mass and a substantial arc to work through, requiring enlargement of the instrument. Furthermore, when the endoscope is tilted, the axis of rotation of the pendulum is no longer horizontal. Now there must be bearings to support the pendulum, and the component of the force of gravity acting on the pendulum is reduced. Even worse, when the slope is very steep, a mechanical pendulum may not receive a sufficient force to seek the vertical.

Sometimes, however, there may be reasons to attach the endoscope such that it cannot rotate with respect to the camera. Or, alternatively, it may be desirable to embed the video camera within the endoscope housing. In these circumstances it is not possible to manually rotate the camera with respect to the endoscope, so some other means is necessary to right the displayed image. Furthermore, it is desirable to have this image rotation occur automatically so that, regardless of the physical orientation of the endoscope-camera in space, the displayed image of an object will always be correctly oriented with respect to the viewer's reference frame.

In addition to the rotation effects, a further perspective distortion occurs from the difference between viewing the objects directly in three-dimensions with the eyes and on a two-dimensional camera image. This perspective distortion occurs when the endoscope/camera combination views an object from a vantage point that is above (or below) and to the side, relative to the surgeon's direct "line-of-sight." The vanishing point of the perspective view is on the side of the rendered object furthest from the endoscope's vantage point. This results in objects closest to the endoscope end appearing disproportionately large.

U.S. patent application Ser. No. 60/155,850 of Chatenever discloses a device for correcting for the rotation of the endoscope's distal end. That invention uses a single accelerometer to determine the angular displacement of the endoscope using the direction of gravity for a vertical reference.

U.S. Pat. No. 5,881,321 to Kivolowitz, Mar. 9, 1999, discloses a system for using absolute position of a hand-held camera by use of inertial sensors incorporated into the structure of the camera to detect the movement of the camera along three orthogonal axes, as well as angular rotation around the three axes. This device uses a wireless communication device for transmitting the position data and remote processing to alter the generation of images. The wireless communication approach, while appropriate for the larger video or motion picture camera contemplated therein, adds considerable circuitry and therefore size which is unavailable in the tight quarters required in an endoscope. Additionally, no provision is disclosed for mechanical alignment of the image prior to the processing for display.

BRIEF DESCRIPTION OF THE INVENTION

In accordance with one aspect of the current invention, as an endoscope is rotated during usage, the disclosed invention provides signals for an image display that is rotated to compensate for the rotation of the endoscope. In this manner the displayed image does note rotate as the surgeon rotates the endoscope.

Inertial sensors, such as accelerometers or gyroscopes, are employed to provide a signal proportional to the angular rotation of the endoscope. A microprocessor or other electronic circuitry calculates a compensating rotational signal from the proportional signal. The compensating rotational signal is used to re-orient the received image.

In this aspect of the invention the image received from the endoscope distal end may be rotated in three ways: physical rotation of the image sensor; optical rotation of the received image prior to incidence upon the image sensor, and; electronic rotation of the image sensor signals. Physical rotation of the image sensor is accomplished by having the sensor rotatably attached to the endoscope. The compensating rotational signal drives a motor or similar device to rotate the image sensor in a direction opposite to the rotation of the endoscope.

Optical rotation of the received image is accomplished by interposing an optical device between the image received from the endoscope distal end and the image sensor. The optical device is of such a construction that an image viewed through the device appears to rotate as the device is rotated. Certain prisms such as the Pechan prism have this characteristic. The compensating rotational signal drives a motor or similar device to rotate the optical device in a direction so as to compensate for the rotation of the endoscope thereby rotating the image that is incident upon the image sensor.

In another aspect of the present invention, the view presented by the video display can store a preset angle to accommodate what the surgeon needs to see along the axis of the instruments while conducting his procedure within the body cavity. The compensating rotational signal is modified to provide an image orientation that is preferred by the surgeon. This user supplied value is employed by the microprocessor as an offset to the display image rotation provided by the inertial sensors. This allows the surgeon to have the displayed image rotated to any desired orientation and have the invention maintain the image in that orientation.

BRIEF DESCRIPTION OF THE DRAWINGS

FIG. 5 is a schematic diagram illustrating an apparatus and control system of an alternative embodiment of the invention;

FIGS. 6A and 6B is a phasor diagram of an image incident on a Pechan prism;

DETAILED DESCRIPTION OF THE INVENTION

Figure 1:
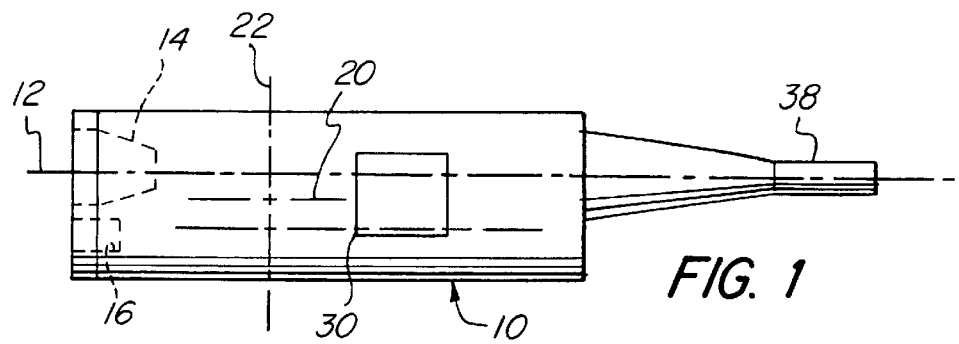
FIG. 1 is a side view of an endoscope useful with this invention.

With reference to FIG. 1, frame 10 has two receptacles 14 and 16 adapted to receive an endoscope cable (not shown), which may be releasable or permanently attached to the frame. A light source provides illumination through receptacle 16 to the proximal end of the endoscope cable. The light is reflected off the walls of an internal body cavity to an image forwarding system of the endoscope cable at the distal end and the light received at receptacle 14 about a central optical axis 12. The light received may be directly, or through a series prisms and lenses, made incident upon an image sensor 30 disposed within the frame 10. The image sensor 30 output image signals are provided through an exit cable 38 for further processing and display on a video monitor. Frame 10, in its upright position, has a lateral horizontal axis 20 and an upright axis 22 that is vertical in the gravitational field. Axes 20 and 22 are normal to each other. U.S. patent application Ser. No. 60/155,850 of Chatenever has a more complete description of an endoscope and is included herein by reference thereto.

In this aspect of the present invention, applying an automatic compensating angular rotation to the video display image minimizes distracting effects of endoscope rotation on the video display. First the angular orientation of the image sensor is determined. Second, this angular change is used to re-orient, or compensate, the video display image thereby stabilizing the display image.

Here it will be noted that the endoscope when in use will have freedom to tilt in all directions. When the endoscope is rotated around its axis the image displayed on the video display will also rotate. This motion is distracting to the surgeon. Worse, when the endoscope rotates clockwise the video display image will rotate counterclockwise. This result is described herein below with respect to FIGS. 2A and 2B.

Figure 2A:
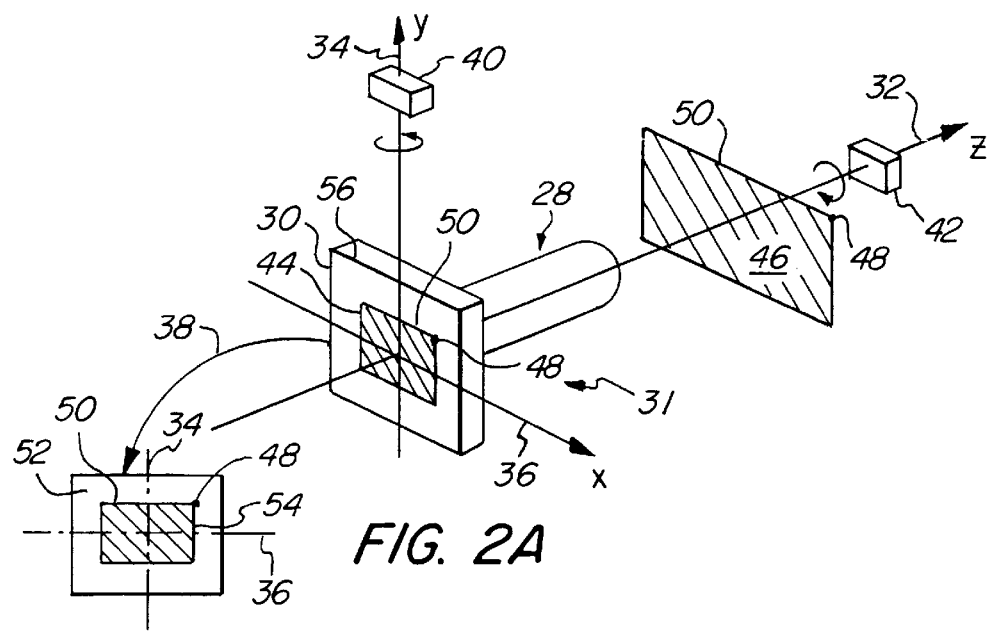
FIG. 2 is a schematic view of the image orientation in accordance with the invention.
Figure 2B:
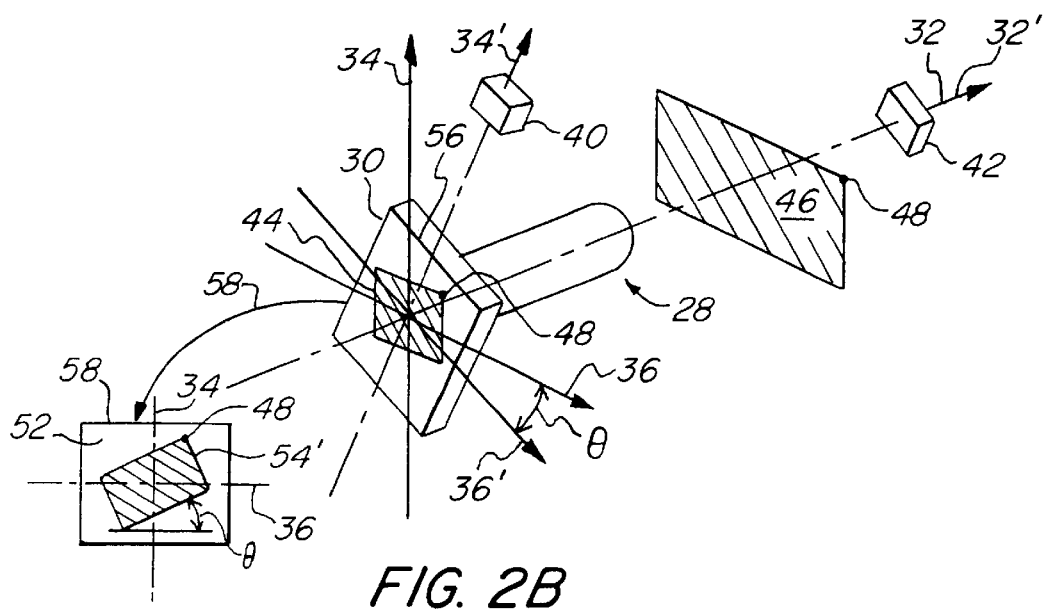

FIGS. 2A and 2B illustrate the effects of endoscope 28 rotation on the video display. Referring to FIG. 2A, the orientation of an image sensor 30 is described by a three orthogonal axis system 31: a z-axis 32 is defined as coincident with the optical axis of image sensor, a y-axis 34 is coincident with the direction of gravity, and an x-axis 36 is orthogonal to a plane defined by x-and z-axes. Image sensor 30 may be a CCD or similar optically sensitive device or system. The image sensor 30 may rotate in any of the three planes determined by orthogonal axis system 31. Deviation in the x-y plane is defined as "image rotation;" deviations is the y-z together with deviations in the x-z plane result in image obliqueness described further herein below with respect to FIG. 9.

FIG. 2A illustrates an endoscope 28 with image sensor 30 capturing an image 46. For illustrative purposes, both image sensor 30 and image 46 are rectangles orthogonal in the x☐y plane. A sensor projection 44 depicts image 46 as projected onto image sensor 30 and coordinate axis 31. The image sensor 30 outputs on a line 38 the electronic representation of image 46 to a video display 52. Video display 52 has vertical axis 34 and horizontal axis 36 respectively parallel to y-axis 34 and x-axis 36. Display image 54 on video display 52 is representative of image 46 as viewed by image sensor 30 and presents a rectangle. Note the position of image 46 corner 48 as projected onto image sensor 30 and displayed on video display 52. Corner 48 appears on a horizontal line 50 of image 46 closest to the top edge 56 of image sensor 30. FIG. 2B illustrates endoscope 28 with image sensor 30 rotated through an angle theta, Θ. Image 46 has not rotated so projection 44 onto coordinate axis 31 is the same as in FIG. 2A with corner 48 located as before. Since image sensor 30 has rotated, corner 48 is located closer to image sensor 30 top edge 56. Therefore, corner 48 is displayed as closer to top edge 58 of display 52. It is now seen that while image sensor 30 rotates clockwise through angle Θ, a displayed image 54' has rotates counterclockwise through the same angle.

In this aspect of the present invention, a plurality of inertial sensors 40 and 42 are used to monitor the angular orientation of image sensor 30 with respect to orthogonal axis system 31. For the purposes of illustration, these sensors are shown as a y-sensor 40, and a z-sensor 42. The usage of two types of inertial sensors is described: accelerometers used as gravity detectors and gyroscopes used as angular displacement detectors. Once the angular orientation of image sensor 30 is determined, the display image 54' may be rotated an essentially equivalent amount in a compensating direction.

In a first embodiment, two accelerometers are used to determine angular rotation of image sensor 30 about its optical z-axis 32. When in use, the endoscope will have freedom to tilt in all directions so that the accelerometer will often be responding to a component of vertical gravitational force that is considerably less than its maximum value. In some instances the camera enters the anatomy at an angle that is so extreme that it becomes difficult to determine, by use of a single gravity sensor, in which direction or how much of an automatic angular compensation is required. For example, when z-axis 32 is depressed 60 degrees, the vertical component of gravity to which first accelerometer 42 refers while keeping the image upright is much less than maximum gravity force. The second accelerometer 40 is oriented so that the vertical component of gravity upon it increases as z-axis 32 is depressed. Thus the angular offset required can be derived from the two accelerometers 40 and 42. It is an advantage of the present invention that it can thereby respond properly over a large angular range.

In an alternative embodiment, a single rate gyroscope (gyro) can be used as the inertial sensor 42 in FIG. 2. This embodiment obviates the need for an additional sensor 40. The gyro output is used to determine the offsetting rotational requirement. A gyro creates a force proportional to the angular displacement relative to its axis of rotation. The gyro does not produce such a force if the axis of rotation is merely translated. For example, a gyro having an axis of rotation parallel to the x-axis will produce a force in response to an attempt to angularly displace the axis around either the y or z orthogonal directions. Hence, a gyro in this example provides a force proportional to the angular displacement in the y-z plane.

It is to be observed that in either the two-accelerometer or the single gyro embodiment, a signal is developed that represents the angular rotation of image sensor. Usage of that signal to provide angular rotation compensation of the video display image may be achieved through alternative embodiments of the present invention and it is to these alternative embodiments that we now turn our attention.

Figure 3:
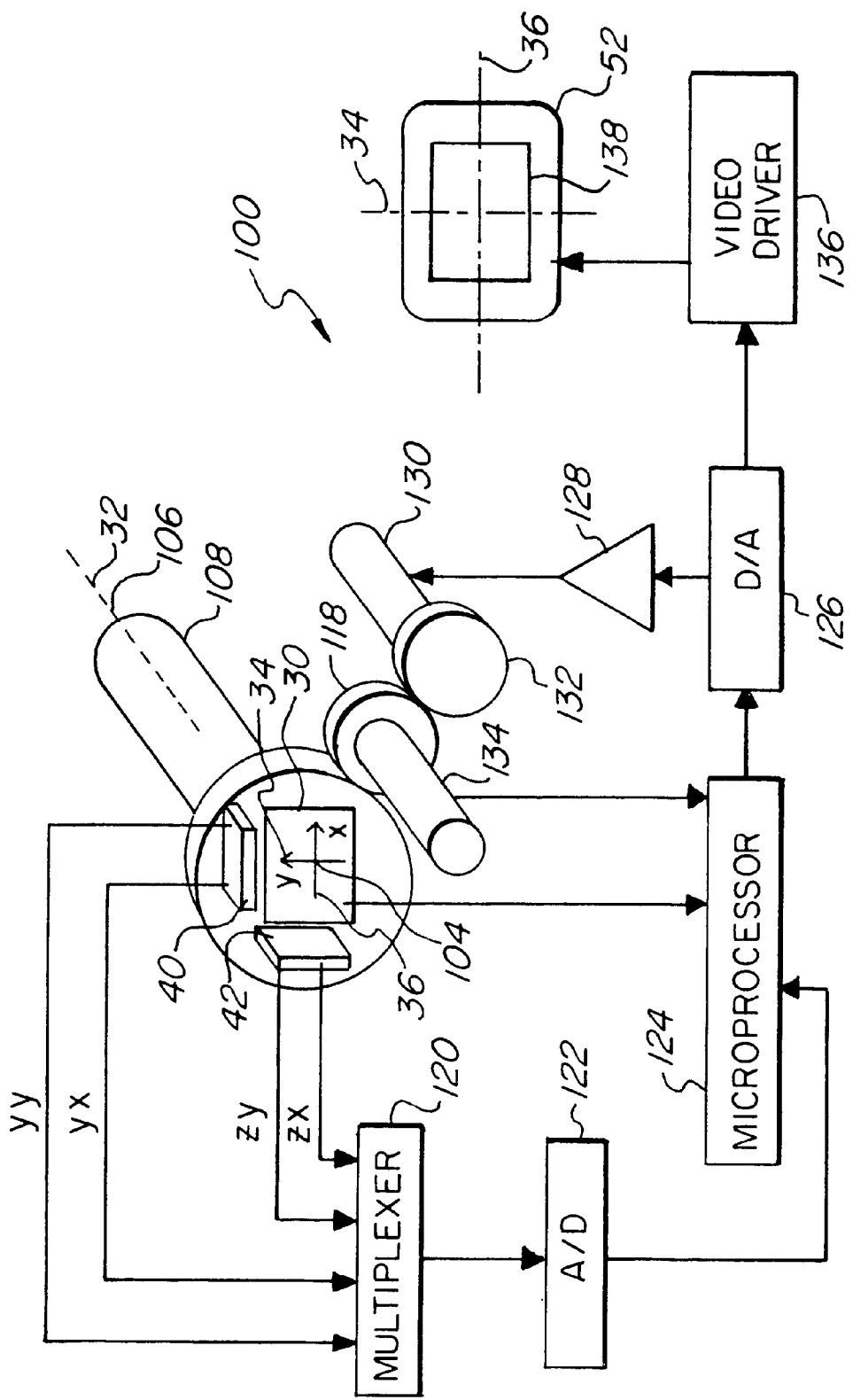
FIG. 3 is a schematic diagram illustrating the apparatus and control system of a first embodiment of the invention.

FIG. 3 illustrates an apparatus 100 to automatically compensate for various angular orientations of an endoscope optical axis 106 according to the present invention. An image sensor 30 is rotatably mounted to the endoscope frame (not shown). Image sensor 30 center point 104 may be located on optical axis 106 of the image forwarding system of the endoscope or optical axis 106 may be redirected by prisms through center point 104. Image sensor 30 is rotatable around its center point 104. Image sensor 30 has its own lateral axis 36 and upright axis 34. Upright axis 34 is aligned with the direction of gravity.

A first inertial sensor 40 for sensing rotation of the camera around the y-axis is rotatably mounted to the frame. In a similar manner a second inertial sensor 42 for sensing rotation of the camera around the z-axis 32 may be rotatably mounted to the frame. Both sensors 40 and 42 are in a fixed spatial relationship and rotate with image sensor 30. Most conveniently, the sensor(s) is directly bonded to image sensor 30. A rotational driver 118 can serve to journal inertial sensors 40, 42 and image sensor 30.

In the case where inertial sensors 40 and 42 are accelerometers, two signals for each sensor corresponding to y-axis and z-axis accelerometer outputs, respectively, are applied through a multiplexer 120 to an A/D converter 122. The resulting digital signals are applied to a microprocessor 124 together with the output signals from image sensor 30. Microprocessor 120 analyzes the y and z signals and derives an angular rotation compensating signal that is supplied to a D/A converter 126. The output of D/A converter 126 is applied through an amplifier 128 to drive a motor 130. Motor 130 is bi-directional to rotate rotational driver 118 that in turn journals image sensor 30 and accelerometers 40 and 42.

A motor output driver 132 is affixed to the output shaft of motor 130. Rotation of motor 130 rotates motor output driver 132 which in turn rotates a rotational driver 118. The rotational driver 118 is fixed on the shaft of an encoder 134. Encoder 134 applies a servo signal feedback to microprocessor 124. Microprocessor 124 interprets the feedback signal to determine whether further accelerometer rotation is required. As a result, image sensor 30 is rotated about its optical axis so that upright axis 34 is re-aligned with the direction of gravity.

Alternatively, a rate gyro can be used to replace both accelerometers 40 and 42. Unlike an accelerometer, a gyro will require initialization in order to align its axis of rotation with either the direction of gravity or lateral axis 36 of image sensor 30. The gyro output is used to determine the offsetting rotational requirement that is applied to multiplexer 120 and thence to A/D 122 and microprocessor 124. Microprocessor 124 causes journaling of image sensor 30 in the same manner as described herein above until the gyro outputs an equal and opposite signal indicating that image sensor 30 has journaled back to its original position.

Microprocessor 124 operates on the signal provided from image sensor 30 and applies a signal to a video driver 136 that in turn provides a signal to drive a video display 52. This display will ordinarily be placed on a shelf or be held by a bracket on a wall or a ceiling. Video display 52 has an upright axis 34 and a lateral axis 36. These axes will generally be viewed as vertical and horizontal. If the image sensor 30 is maintained upright, then the display axes will coincide with the image sensor axes. It will now be seen that rotating the image sensor to maintain its axes in a nominally horizontal and vertical alignment will provide the same orientation to the image on the screen whatever the rotational position of the endoscope may be. As a consequence, the surgeon will remain in a fixed spatial orientation relative to the operating site. He need not exert efforts to orient himself relative to an image that rotates on the display.

As a further advantage, this arrangement displays the full area of the field available from the image sensor. The aspect ratio of the screen and of the image sensor is the same. If the image were rotated, corners and some of the edges of the screen would be blank. Possibly important information from the corners of the image sensor could be lost. This invention does not suffer this risk.

In yet another embodiment of this aspect of present invention, the surgeon may apply a rotational offset to the display image. In this case the surgeon has a preferred viewing angle of the surgical site. The rotational offset is an external value stored by the microprocessor that compensates for angular rotation of the image sensor back to the surgeon's preferred viewing angle.

Figure 4:
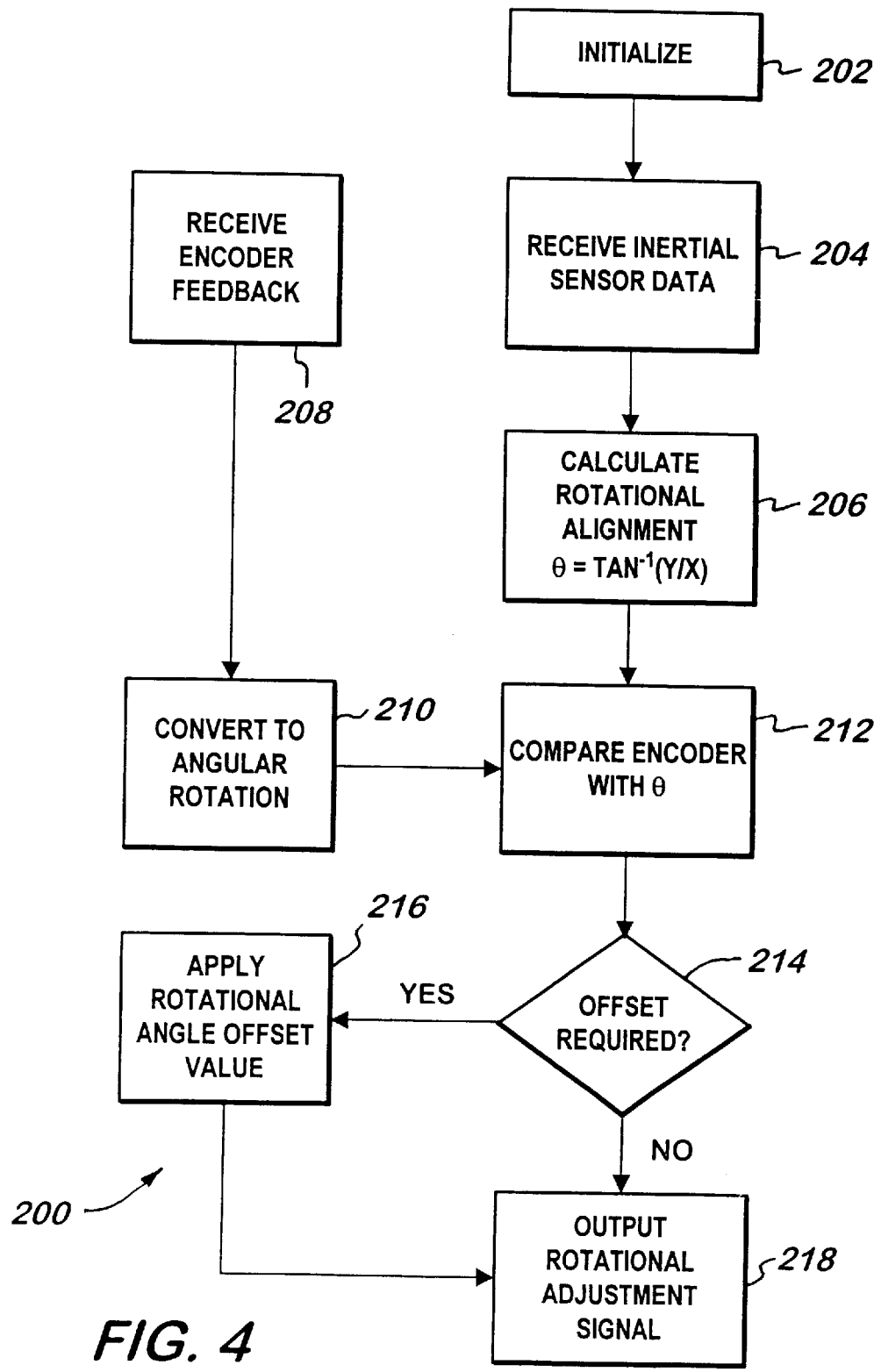
FIG. 4 is a functional flowchart of the control of the of the first embodiment of the invention.

FIG. 4 illustrates a flowchart 200 of the data calculations of the embodiment of FIG. 3. Initialization of circuit elements is accomplished at step 202. In particular, signals are provided and received to assure that any gyros have reached equilibrium and the gyro axis is aligned with either the image sensor lateral or upright axis as necessary. In operation, inertial sensor signals are received at step 204. Based upon these signals, a microprocessor calculates the rotational angle q of the image sensor at step 206. Received at step 208 is the output of the encoder. This output is converted into an equivalent encoder rotational angle at step 210 and compared with the image sensor rotational angle at step 212. Based upon this comparison the microprocessor determines if further image sensor rotation is required. In step 214 the system determines whether a particular offset relative to the angle q is required by the surgeon. If so then this is introduced at 216 by varying the angle q. The microprocessor then outputs a signal for rotational adjustment of the image sensor axis to cause a desired alignment of the display.

Referring to FIG. 5, an alternative embodiment 300 is illustrated wherein the optical image is rotated before reaching the image sensor 304. In this embodiment, the optical image is rotated rather than the image sensor, to accommodate angular rotation of the endoscope about its optical axis. In an illustrative example of this invention, a prism 302 is interposed between the return of the image from the endoscope's distal end 338 and an image sensor 304 at the proximal end. Prism 302 is of a design that rotation of the prism causes a rotation of an output image for a fixed input image and is described in further detail herein below. An object lens 306 for focusing of the optical image on image sensor 304 may be interposed between prism 302 and image sensor 304. Prism 302 is fixedly disposed on a rotating member 308 whereby a rotation of rotating member 308 rotates prism 302 an equivalent angular amount. For simplicity, prism 302, object lens 306, and image sensor 304 are all shown aligned along the same axis. Other lens and prism arrangements may be used to direct the optical image as necessary. A microprocessor 310 receives an angular rotation signal on a line 340 from an inertial sensor (not shown) attached to prism 302 (or prism rotating member 308) that is proportional to the angular displacement of the optical axis of prism 302. Microprocessor 310 outputs an rotational adjustment signal to an amplifier 312 which amplifies the signal to provide an electrical drive for a motor 314. A first driver 316 is affixed to the motor output shaft 315 and is operably connected to a second driver 318 which is in turn operably connected to rotating member 308. Hence motor 314 output rotation is transferred via drivers 316 and 318 to cause journaling of rotating member 308 and prism 302 affixed thereon.

Second driver 318 is mounted on an encoder shaft 320 of an encoder 322 whereby rotation of second driver 318 causes rotation of encoder shaft 320. Encoder 322 provides an image rotation signal on a line 324 that is proportional to shaft 320 rotation. Image rotation signal 324 provides feedback to microprocessor 310 for determining when prism 302 has rotated a sufficient amount to countervale the output from the inertial sensor (not shown).

A Pechan prism, well known to those of ordinary skill in the art, is an example of a prism having the rotational characteristics desired and is illustrated in top view as 326 in FIG. 6A and front view 327 in FIG. 6B. The prism has an optical axis 328. Surfaces 334 and 336 are silvered. An input image 330 to Pechan prism 326 results in an output image 332 that is rotated through an angle of p radians (180°) about optical axis 328 and that is also rotated through an angle of p radians (180°) about an axis perpendicular to optical axis 328. It is a feature of the Pechan prism that rotation of the prism about its optical axis causes the output image to rotate at twice the angular velocity with respect to the rotation of the prism.

Figure 7:
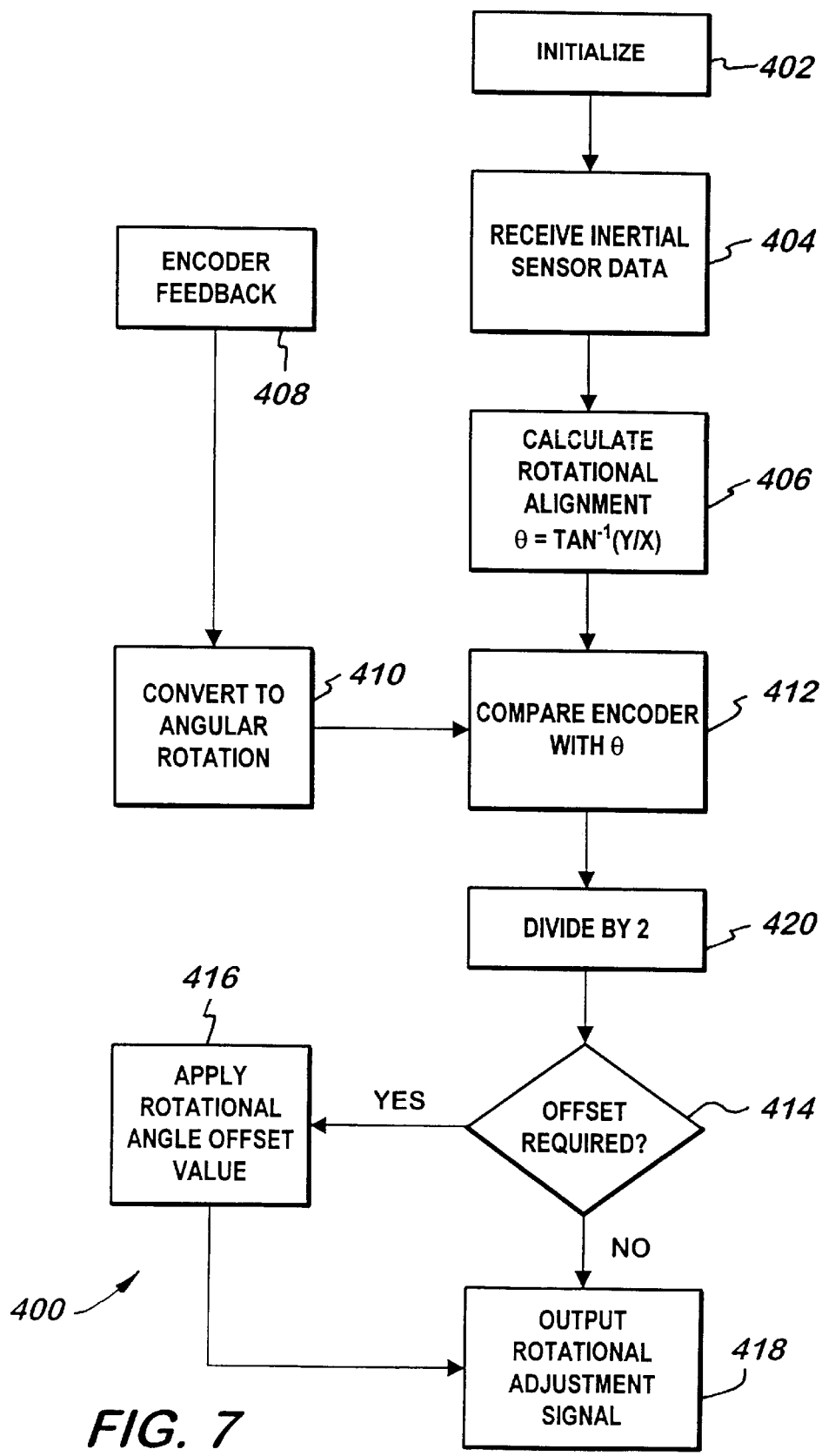
FIG. 7 is a flowchart of the control steps of the of an alternative embodiment of the invention.

FIG. 7 illustrates a flowchart 400 of the data calculations of the embodiment of FIG. 5. Initialization of circuit elements is accomplished at step 402. In particular, signals are provided and received to assure that any gyros have reached equilibrium and the gyro axis is aligned with either the image sensor lateral or upright axis as necessary. In operation, inertial sensor signals are received at step 404. Based upon these signals, a microprocessor calculates the rotational angle q of the image sensor at step 406. Received at step 408 is the output of the encoder. This output is converted into an equivalent encoder rotational angle at step 410 and compared with the image sensor rotational angle at step 412. Based upon this comparison the microprocessor determines if further image sensor angular rotation is required. The calculated image sensor angular rotation is divided by two (2) in step 420. This division is necessary because it is a feature of the Pechan prism that rotation of the prism about its optical axis causes the output image to rotate at twice the angular velocity with respect to the rotation of the prism. In step 414 the system determines whether a particular offset relative to the angle q is required by the surgeon. If so then this is introduced at 416 by varying the angle q. The microprocessor then outputs a signal for rotational adjustment at step 418 of the image sensor axis to cause a desired alignment of the video display.

Figure 8:
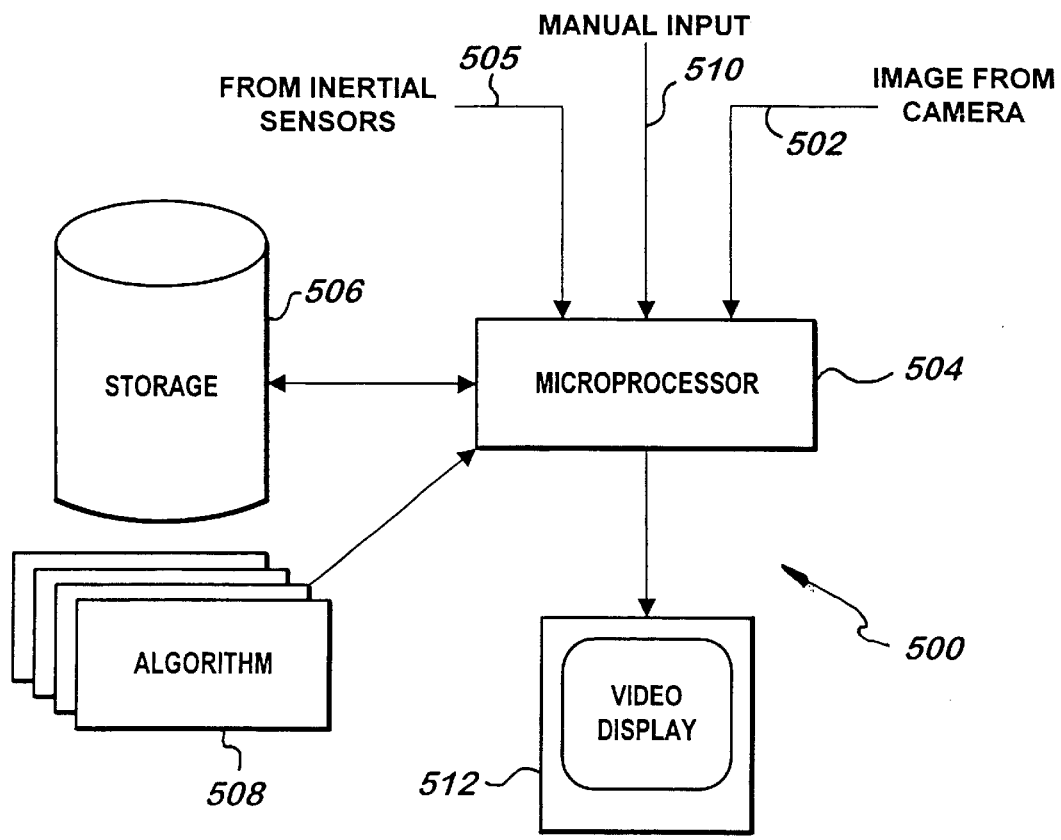
FIG. 8 is a diagrammatic representation of an electronic correction for a rotation of an image sensor about its optical axis.

In yet another embodiment, the change in rotational alignment of the display can be done electronically within a microprocessor as shown diagrammatically as 500 in FIG. 8. The image sensor image 502 is received by a microprocessor 504, digitized and stored in a storage medium 506. Microprocessor 504 receives the relative angular rotation requirement, q, from the inertial sensors on a line 504. Microprocessor 504 retrieves the digitized image from storage medium 506 and adjusts each part of the image for the rotation requirement in accordance with an appropriate affine algorithm 506. An external rotational offset 510 may also be input to microprocessor 504 to establish a vertical image offset view preferred by the surgeon. This manual input is used as an offset in algorithm 508. The result of the algorithm is used to drive the video display 512 to present a display image orientation corrected for the relative angular rotation requirement.

In yet another exemplary embodiment of the present invention, corrections may be made for image distortions due perspective variations. These perspective variations result from the obliqueness of the endoscope's distal end with respect to an image. The obliqueness of an image is determined by ascertaining an angular orientation of the image sensor in both the x-z and y-z planes as distinguished from the rotational adjustment for angular variations about the optical axis as previously discussed.

Figure 9A:
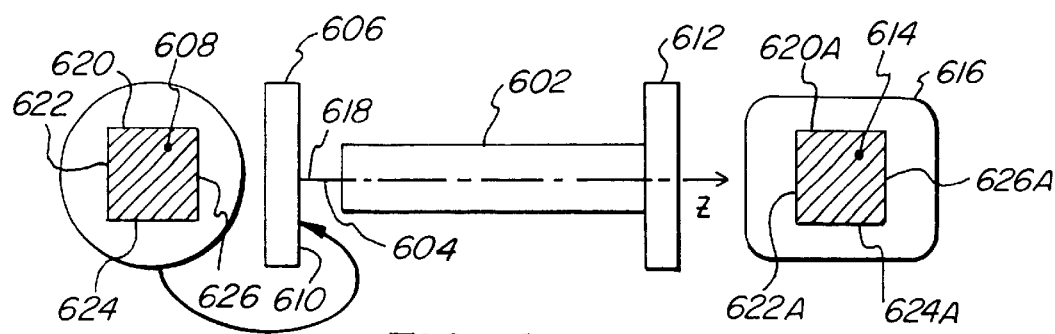
FIG. 9 is a diagram of the distortion of an image on a video display as a result of the oblique orientation of an image receiving device to an image.
Figure 9B:
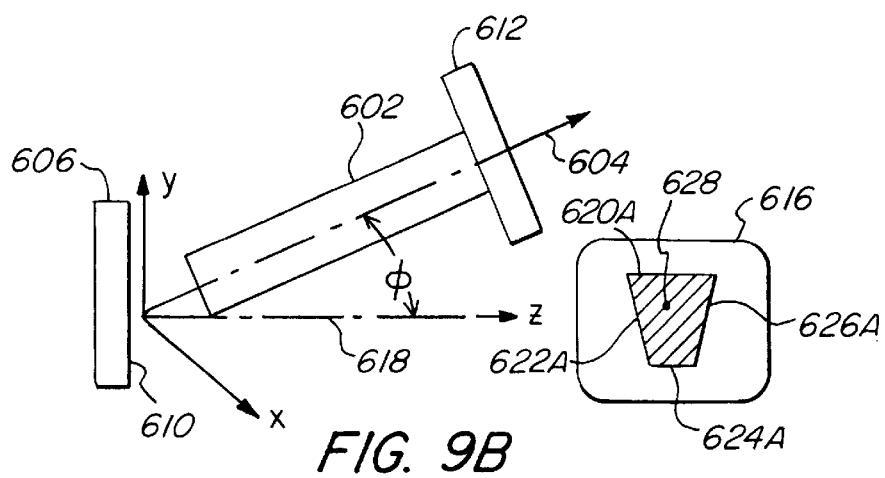
Figure 9C:
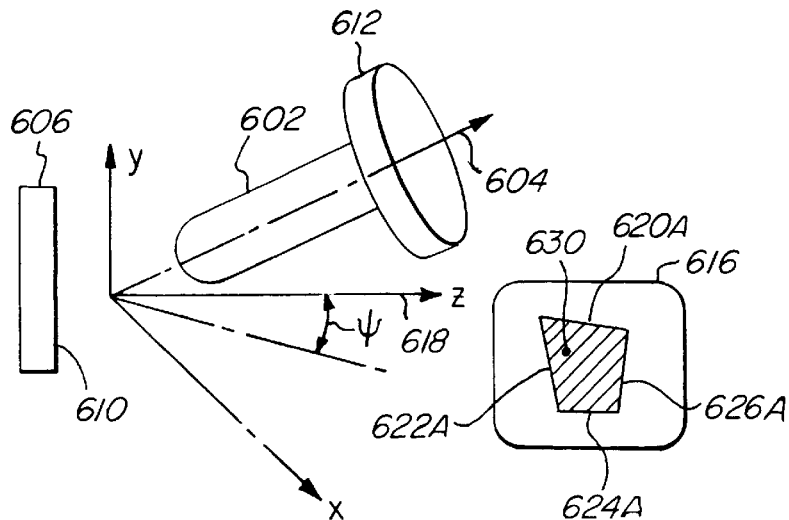

FIG. 9A–C illustrate the difficulty associated with the "obliqueness" of a view causing a "perspective distortion" on the visual display. Referring to FIG. 9A, an endoscope image forwarding system 602 is shown wherein an optical axis 604 of forwarding system 602 is coincident with a horizontal z-axis 618 and is perpendicular to an image surface 606. An image of a square 608 is an illustrative actual view 610 of endoscope 602 to illustrate the perspective distortion. Square 608 has sides 620, 622, 624, and 626. An image sensor 612 receives actual image 610 and a resultant image 614 is shown on a video display 616. Resultant image 610 accurately reflects actual view 610 because of the perpendicular relationship between optical axis 604 and image surface 606. Resultant image 614 has sides 620A, 622A, 624A, and 626A corresponding to sides 620, 622, 624, and 626 of square 608, respectively.

In FIG. 9B optical axis 604 of endoscope 602 is raised by an angle, phi, above horizontal axis 618. Image sensor 612 receives a perspective view of actual square image 610. That is, actual image 610 will appear to have a first vanishing point below image surface 606. Lines that do not converge at the vanishing point, such as line 620, which are closer to the end of the endoscope 602 will appear longer than those further away such as line 624. Lines converging at the vanishing point, such as lines 622 and 626, will appear foreshortened. Image sensor 612 will receive this view and a resultant display 628 is shown on video display 616. Square 608 appears as a trapezoidal shape 628 on video display 616. Side 620A appears longer than side 624A and sides 622A and 626A appear foreshortened.

In FIG. 9C, in addition to being raised above horizontal axis 618, optical axis is 604 of endoscope 602 is angled away from the y□z plane, by an angle psi. The y□z plane is the plane of the drawing. Actual image 610 will appear to have first vanishing point below and a second vanishing point to the right (or into the paper) of image surface 606. Lines that converge to the first vanishing point below actual image 606, such as lines 622 and 626, will appear foreshortened. Lines which are closer to the end of the endoscope 602, such as line 620 will appear longer than those further away such as line 624. Lines converging at the second vanishing point, such as lines 620 and 624, will appear foreshortened. Lines which are closer to the end of the endoscope 602, such as line 622 will appear longer than those further away such as line 626. Image sensor 612 will receive this view and a resultant display 630 is shown on video display 616. Square 608 appears as an irregular quadrilateral. The result for the surgeon is a warped view wherein side 622A appears higher and longer than side 626A and the two lines are not parallel; side 620A appears longer than 624A and these two lines also appear to be not parallel. This may be disconcerting to a surgeon who expects the anatomy to appear in very specific spatial relationships.

The use of gravity sensing accelerometers will produce the angular corrections necessary. However, just as in the aforementioned optical axis rotation of the x-y plane, two accelerometers are required in each plane to advantageously enable one to define automatic adjustment of the display as derived from the output signals from both accelerometers.

Image modification for obliqueness is done by application of an affine algorithm to a digitally stored image. In addition to the correction for the angular rotation about the x-and y-axes, the algorithm may also include factors to warp or perspective-distort the image, if desired, then display the transformed image on a video display.

Figure 10:
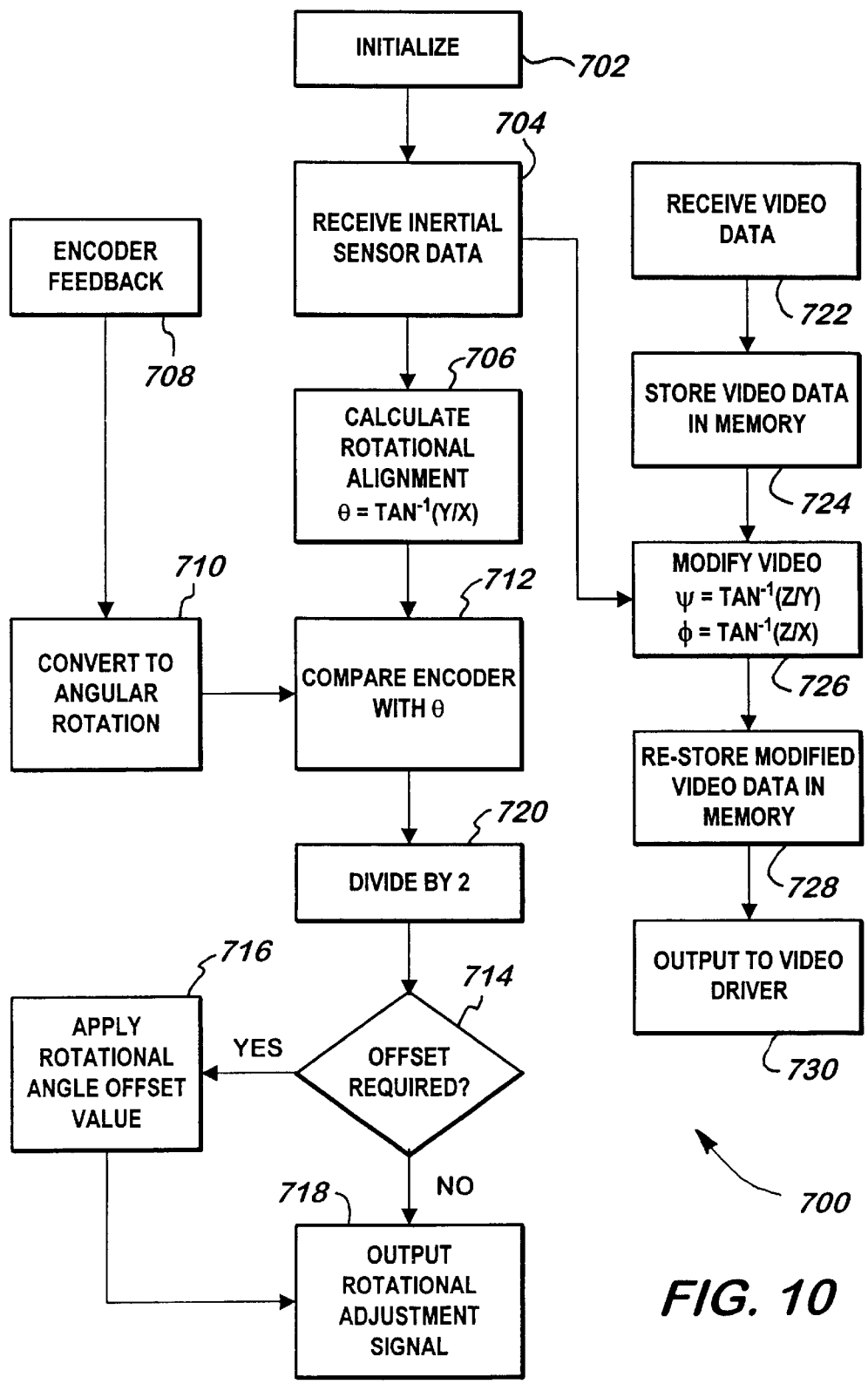
FIG. 10 is a flowchart of the control steps of a third embodiment of the invention wherein both image sensor rotation and perspective distortions are corrected.

FIG. 10 illustrates a flowchart 700 of the data calculations for the perspective distortion caused by an oblique endoscope view of an image as described herein above in FIG. 9. Initialization of circuit elements is accomplished at step 702. In particular, signals are provided and received to assure that any gyros have reached equilibrium and the gyro axis is aligned with either the image sensor lateral, upright, or optical axis as necessary. In operation, inertial sensor signals are received at step 704. Based upon these signals, a microprocessor calculates the rotational angle q of the image sensor at step 706. Received at step 708 is the output of the encoder. This output is converted into an equivalent encoder rotational angle at step 710 and compared at step 712 with image sensor rotational angle calculated at step 706. Based upon this comparison the microprocessor determines if further image sensor angular rotation is required. The calculated image sensor angular rotation is divided by two (2) in step 720 if a Pechian prism is used as described herein above. In step 714 the system determines whether a particular offset relative to the angle q is required by the surgeon. If so then this is introduced at 716 by varying the angle q. The microprocessor then outputs a signal for rotational adjustment at step 718 of the image sensor axis to cause a desired alignment of the display.

Video data is received from the image sensor at step 722. Video data 722 is digitized and stored in computer memory at step 724. Inertial data received at step 704 is used to calculate obliqueness angles psi, Y, and phi, F, at step 726. Digitized video image 724 is retrieved from memory and modified using angles psi, Y, and phi, F, in step 726. Modified video image 726 may be stored again in memory at step 728. Modified video image 726, corrected for perspective distortion is output to a video driver at step 730. The video driver is a device adapted to receive digitized video signals and provide a drive signal for presentation of an image on a video display. Hence, the perspective distortion of an image received from an image sensor is corrected through the application of a mathematical algorithm applied to the received image. Correction for rotation about the optical axis of the image sensor may be accomplished either through a mechanical manipulation of the received video image as described herein above. Alternatively, correction for rotation about the optical axis may also be accomplished through application of a mathematical algorithm to the received video signal from the image sensor.

Figure 11:
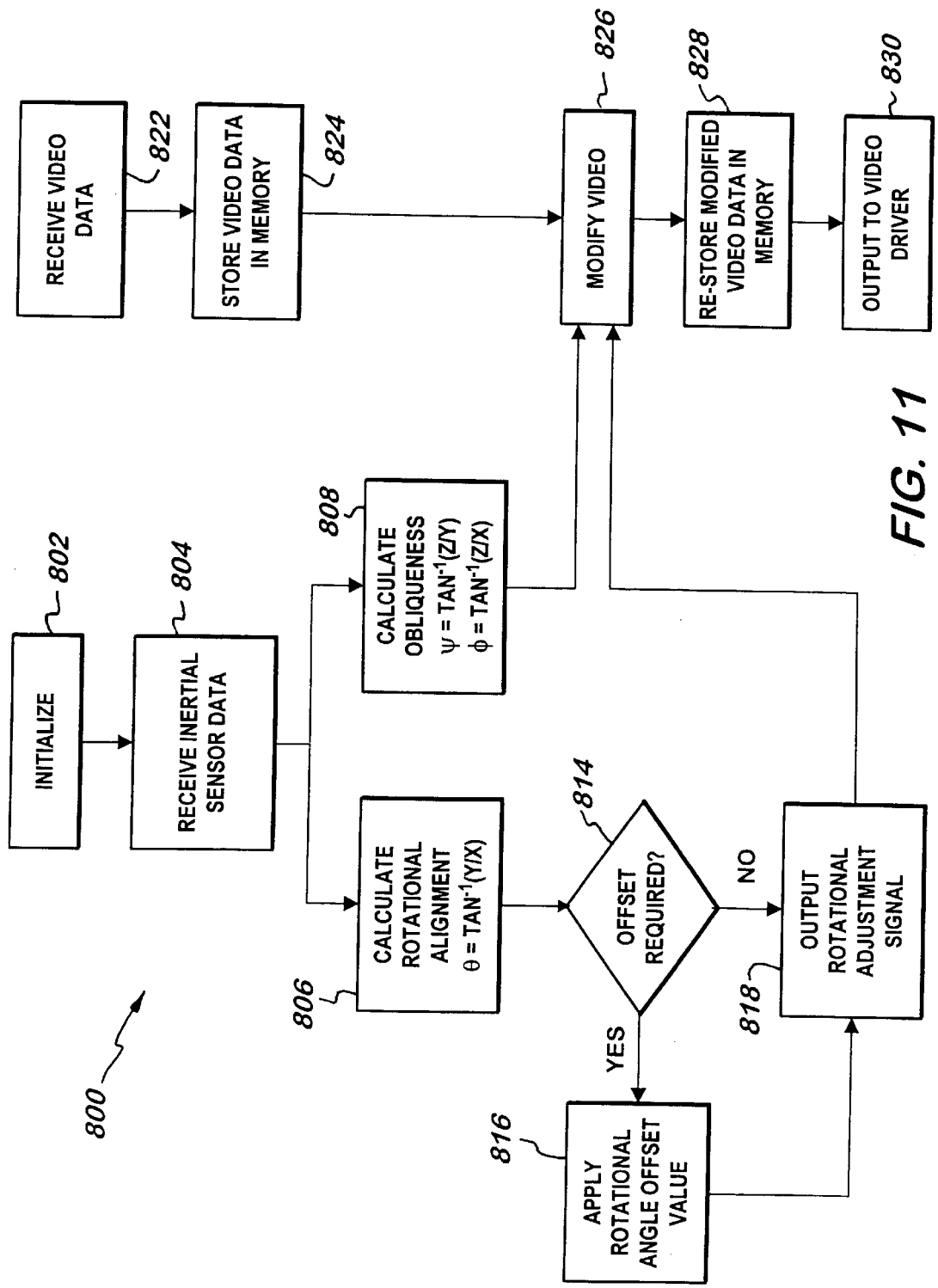
FIG. 11 is a functional flowchart of the control of a fourth embodiment of the invention wherein both image sensor rotation and perspective distortions are corrected by electronic means.

FIG. 11 illustrates a flowchart 800 wherein the data calculations for the rotation of the image sensor about its optical axis as well as the perspective distortion caused by an oblique endoscope view of an image is accomplished by application of mathematical algorithms to the received video signals. Initialization of circuit elements is accomplished at step 802. In particular, signals are provided and received to assure that any gyros have reached equilibrium and the gyro axis is aligned with either the image sensor lateral, upright, or optical axis as necessary. In operation, inertial sensor signals are received at step 804. Based upon these signals, a microprocessor calculates the rotational angle q of the image sensor at step 806 and perspective distortion angles psi, Y, and phi, F, at step 808. In step 814 the system determines whether a particular offset relative to the angle q is required by the surgeon. If so then this is introduced at 816 by varying the angle q. The microprocessor then outputs a signal for rotational adjustment at step 818 of the image sensor axis to cause a desired alignment of the display.

Video data is received from the image sensor at step 822. Video data 822 is digitized and stored in computer memory at step 824. Digitized video image 824 is retrieved from memory and in step 826 is modified using perspective distortion angles psi, Y, and phi, F, calculated in step 808 and rotational adjustment angle theta, q, calculated in step 818. Modified video image 826 may be stored again in memory at step 828. Modified video image 826, corrected for perspective distortion and angular rotation is output to a video driver at step 830. The video driver is a device adapted to receive digitized video signals and provide a drive signal for presentation of an image on a video display. Hence, both the perspective distortion and angular rotation of an image received from an image sensor is corrected through the application of a mathematical algorithm applied to the received image.

In yet another embodiment of the present invention the video image on the video display is enhanced through the usage of color. The current image sensor devices are monochromatic. In order to create a color image, the incident light from the endoscope is divided into three color components, red, blue, and green, for example. Each of the color components is caused to be incident upon a different image sensor. The output of each of the image sensors is digitized and stored. A microprocessor retrieves the digitized images, combines them, and restores them until the entire image is processed in a like manner. Any applicable algorithms required are subsequently applied as described in the various embodiments herein above to modify the image for perspective distortion. The microprocessor then retrieves the image and displays the modified image. Correction for rotation of the endoscope about the optical axis is accomplished by the imposition of a prism as described in FIG. 5 herein above.

Figure 12:
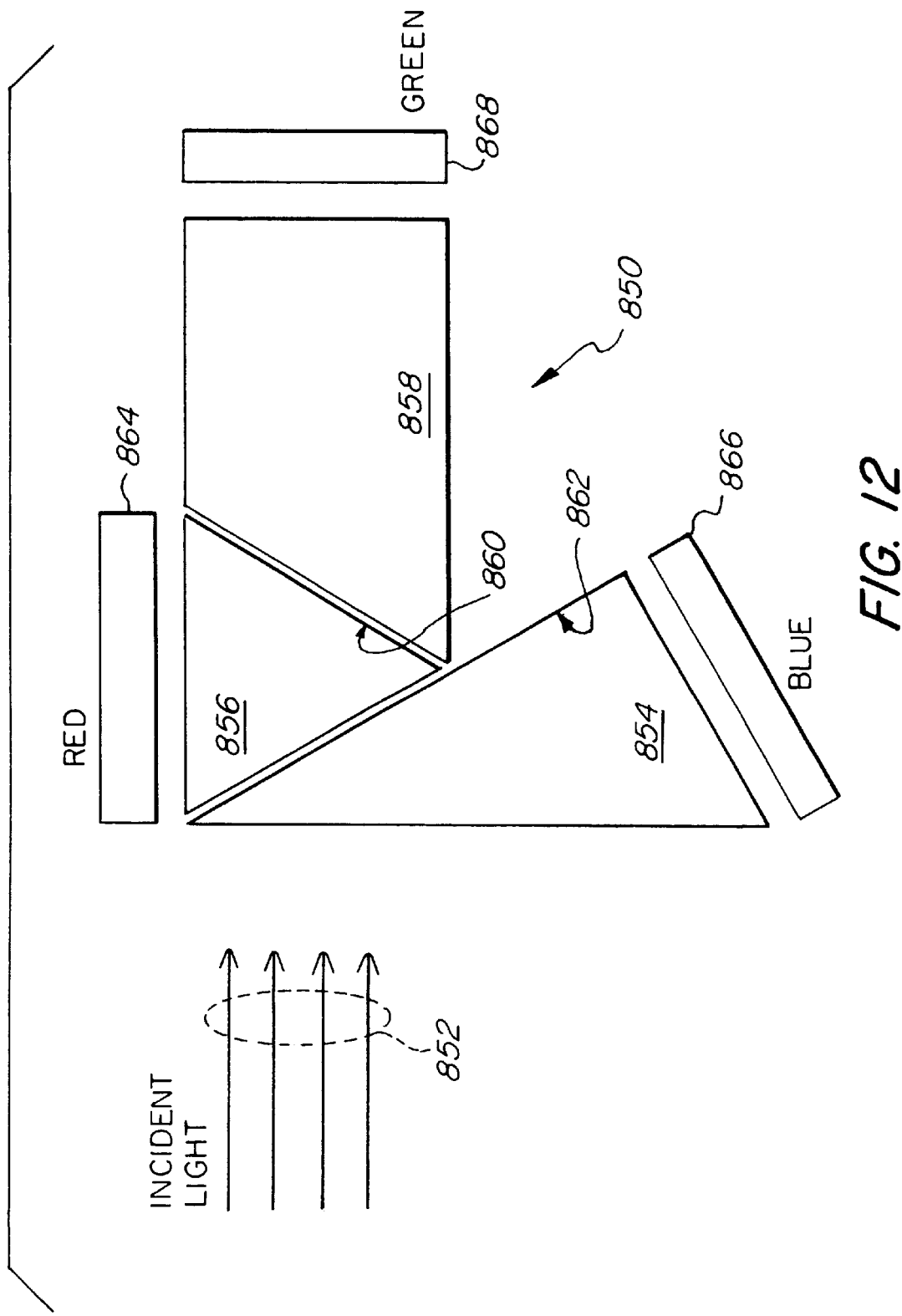
FIG. 12 is a diagram of prisms used to separate incident light into three components of light.

FIG. 12 illustrates an apparatus employing prisms 850 for color separation. Incident light 852 is directed perpendicularly to the surface of a three-part prism comprised of prisms 854, 856, and 858. Surface 860 of prism 856 has a red coating whereby the red component of the incident light is reflected to the red image sensor 864. In a similar manner, surface 862 of prism 854 has a blue coating whereby the blue component of the incident light is reflected to the blue image sensor 866. The remaining component of the light is allowed to pass through the prism 858 to the green image sensor 868. In this manner the incident light is divided into three components.

Figure 13:
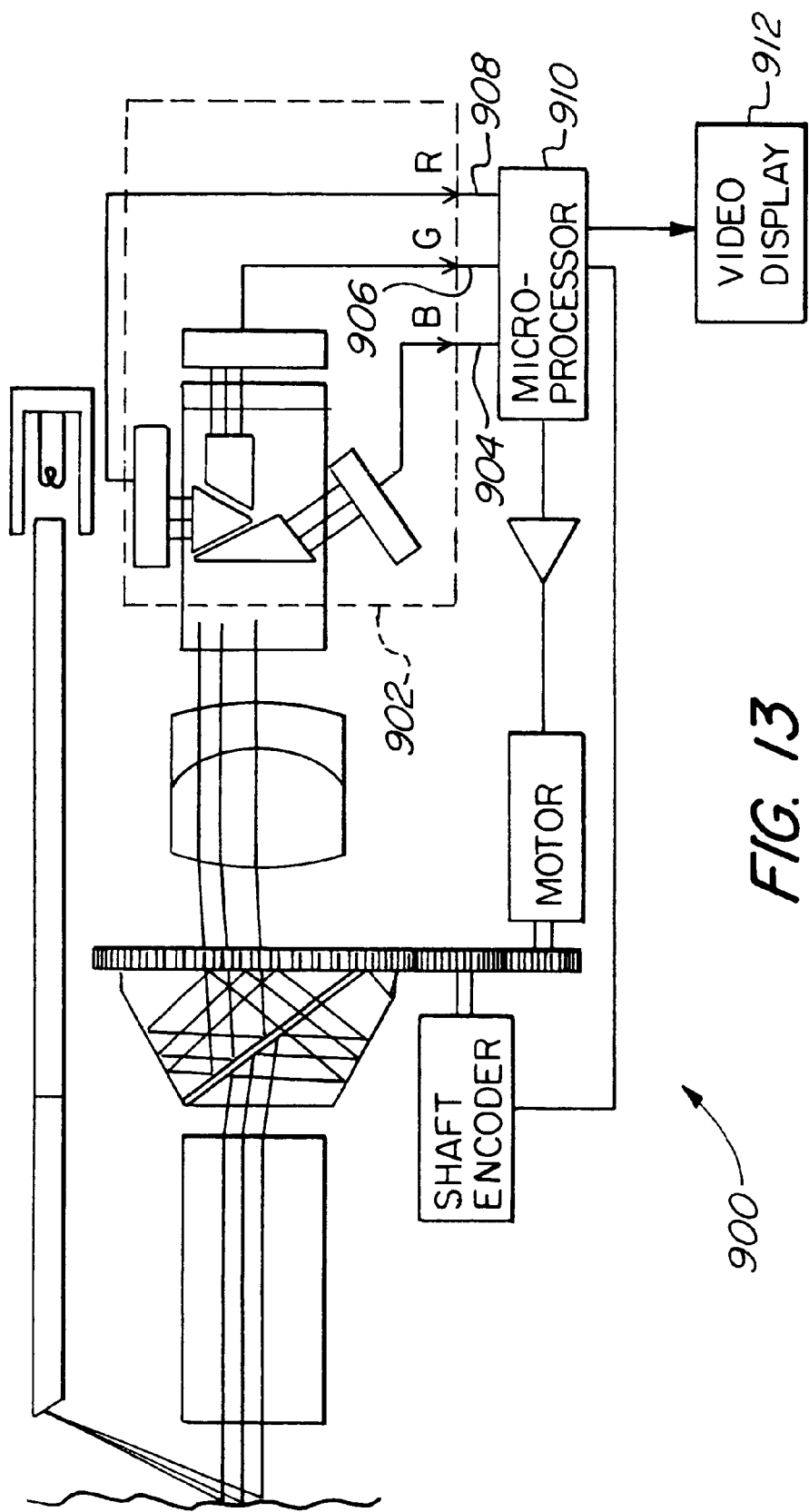
FIG. 13 is a schematic diagram illustrating an apparatus and control system of a fifth embodiment of the invention resulting in a color display.

Referring to FIG. 13, the color separator of FIG. 12 is shown as 902 in the color image sensor system 900. Color separator 902 generates a image sensor signal for each of the color components blue 904, green 906, and red 908. Signals 904, 906, and 908 are received by a microprocessor 910, combined and displayed on a video display 912 as shall described in more detail herein below. The rotational modification is otherwise performed in a manner equivalent to that described in the monochromatic system of FIG. 5.

Figure 14:
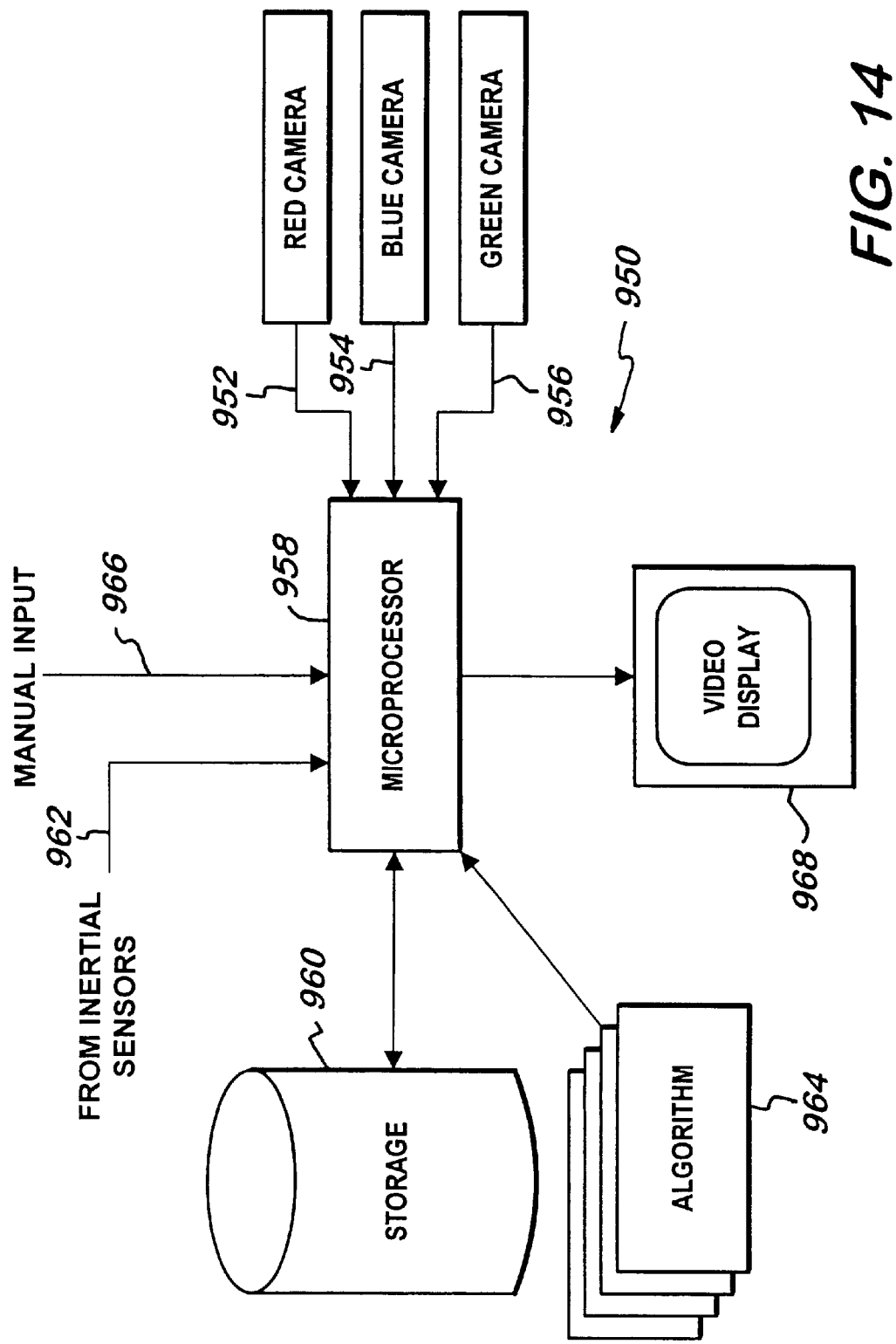
FIG. 14 is a schematic diagram of a control for the fifth embodiment.

FIG. 14 diagrammatically illustrates a color system 950. The image sensor images 952, 954, and 956 are received by a microprocessor 958, digitized and stored in a storage medium 960. Microprocessor 958 also receives the relative angular rotation requirement, q, from the inertial sensors on line 962. Microprocessor 958 retrieves the digitized images from storage medium 960 and combines each picture element in accordance with an appropriate algorithm 964. Rotation of a prism to account for the rotational deviation has been described herein above. An affine algorithm may alternatively be applied in lieu of the prismatic rotational embodiment. A manual input 966 may also be input to microprocessor 958 to establish a vertical image offset view preferred by the surgeon. This manual input is used as an offset in affine algorithm 964. The result of the algorithms is used to drive a color video display 968 to present a color display image orientation corrected for the relative angular rotation requirement.

This invention is not to be limited by the embodiment shown in the drawings and described in the description, which is given by way of example and not of limitation, but only in accordance with the scope of the appended claims.

What is claimed:

1. A video camera system for modifying an image received by an endoscope, comprising:
    a) an image sensor attached to said video camera system, and having a sensor optical axis and a vertical reference, said sensor providing image signals representative of said image;
    b) an optical image rotator rotatably attached to said endoscope between said received image and said image sensor;
    c) at least one inertial sensor for providing a rotation signal representative of angular orientations of said image sensor;
    d) a processor to receive said rotation signal and provide a compensating rotator driver signal derived from said rotation signal and to receive and store a user supplied rotational offset signal to alter said vertical reference of said image sensor; and
    e) an optical image rotator driver being effectively responsive to said compensating rotator driver signal to rotate said optical image rotator to obtain a desired orientation of a display of the image signals.

2. The video camera system of claim 1 wherein said inertial sensor is an accelerometer.

3. The video camera system of claim 1 wherein said inertial sensor includes a plurality of accelerometers, positioned in a predetermined spatial relationship with said image sensor, said spatial relationship being so arranged that at least one of said accelerometers provides a rotation signal for diverse orientations of said image sensor; and
    wherein said processor derives said compensating rotator driver signal from said rotation signals from said accelerometers.

4. The video camera system of claim 3 wherein said plurality of accelerometers comprises two accelerometers.

5. The video camera system of claim 1 wherein said inertial sensor includes at least one gyroscope, having an axis of rotation bearing a predetermined angle relative to said sensor optical axis for providing a rotation signal representative of angular rotation of said image sensor.

6. The video camera system of claim 1 wherein said optical image rotator is a prism.

7. The video camera system of claim 6 wherein said prism is a Pechan prism.

8. The video camera system of claim 1 wherein said inertial sensor includes at least one accelerometer, and wherein said processor derives said compensating rotator driver signal from said rotation signals from said at least one accelerometer.

9. The video camera system of claim 1 wherein said inertial sensor includes at least one gyroscope and at least one accelerometer.

* * * * *

UNITED STATES PATENT AND TRADEMARK OFFICE
CERTIFICATE OF CORRECTION

PATENT NO. : 6,471,637 B1
DATED : October 29, 2002
INVENTOR(S) : David Chatenever et al.

It is certified that error appears in the above-identified patent and that said Letters Patent is hereby corrected as shown below:

<u>Title page,</u>
Item [12] and [75], should read:

-- [12]  Chatenever et al. --

-- [75]  Inventors:   David Chatenever, Santa Barbara, CA
                                  Daniel Mattsson-Boze, Goleta, CA
                                  Marc. R. Amling, Santa Barbara, CA --

Signed and Sealed this

Eighth Day of April, 2003

JAMES E. ROGAN
*Director of the United States Patent and Trademark Office*